United States Patent
Fang et al.

(10) Patent No.: US 7,447,533 B1
(45) Date of Patent: Nov. 4, 2008

(54) IMPLANTABLE ELECTRONIC MEDICAL DEVICE HAVING AN ENCAPSULATED OPTICAL TRANSDUCER

(75) Inventors: Michael Fang, Mountain View, CA (US); Pinida Jan Moolsintong, Palo Alto, CA (US); Casey O'Hara, Belmont, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 671 days.

(21) Appl. No.: 11/090,376

(22) Filed: Mar. 24, 2005

Related U.S. Application Data

(63) Continuation-in-part of application No. 10/672,917, filed on Sep. 25, 2003, now abandoned.

(51) Int. Cl.
*A61B 5/00* (2006.01)
(52) U.S. Cl. .................. 600/310; 607/4; 607/36
(58) Field of Classification Search ............ 607/4, 607/33, 36; 600/325, 339, 515
See application file for complete search history.

(56) References Cited

U.S. PATENT DOCUMENTS

| | | | |
|---|---|---|---|
| 4,262,673 A * | 4/1981 | Kinney et al. ............. 607/5 |
| 5,040,533 A | 8/1991 | Fearnot ............... 128/419 PG |
| 5,556,421 A | 9/1996 | Prutchi et al. ............... 607/36 |
| 5,833,603 A | 11/1998 | Kovacs et al. ............. 600/317 |
| 5,871,513 A * | 2/1999 | Taylor et al. ............... 607/36 |
| 5,913,881 A * | 6/1999 | Benz et al. ............... 607/36 |
| 6,122,536 A | 9/2000 | Sun et al. ............... 600/341 |
| 6,725,092 B2 | 4/2004 | MacDonald et al. .......... 607/2 |
| 6,731,967 B1 | 5/2004 | Turcott ............... 600/407 |
| 2004/0161853 A1 | 8/2004 | Yang et al. ............. 436/164 |

FOREIGN PATENT DOCUMENTS

EP    1 009 278 B1    3/2004
WO   WO 97/01986    1/1997

* cited by examiner

*Primary Examiner*—Eric F Winakur
*Assistant Examiner*—Etsub D Berhanu
(74) *Attorney, Agent, or Firm*—Steven M. Mitchell

(57) ABSTRACT

An implantable electronic device has a main housing with a leak-proof-sealed housing chamber containing electronic circuitry. An optical module is connected to the main housing, and has a module housing with a leak-proof-sealed transducer chamber isolated from the main housing chamber. The module housing has an optically-transmissive optical element, and the transducer chamber contains an optical transducer connected to the circuitry. The module housing includes a number of signal conductors extending from the transducer chamber to a location external to the transducer chamber, and connected to circuitry in the main housing chamber.

20 Claims, 8 Drawing Sheets

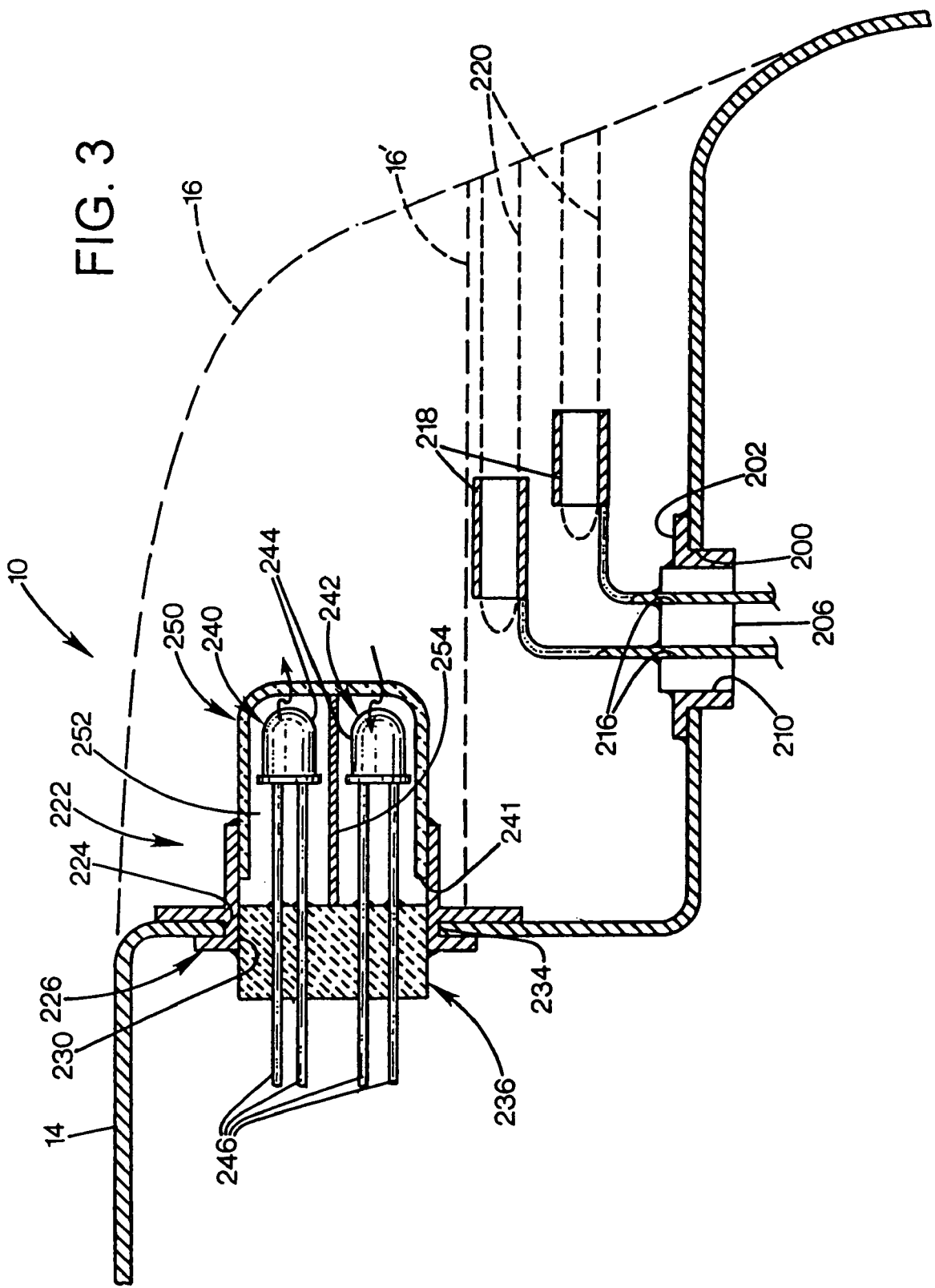

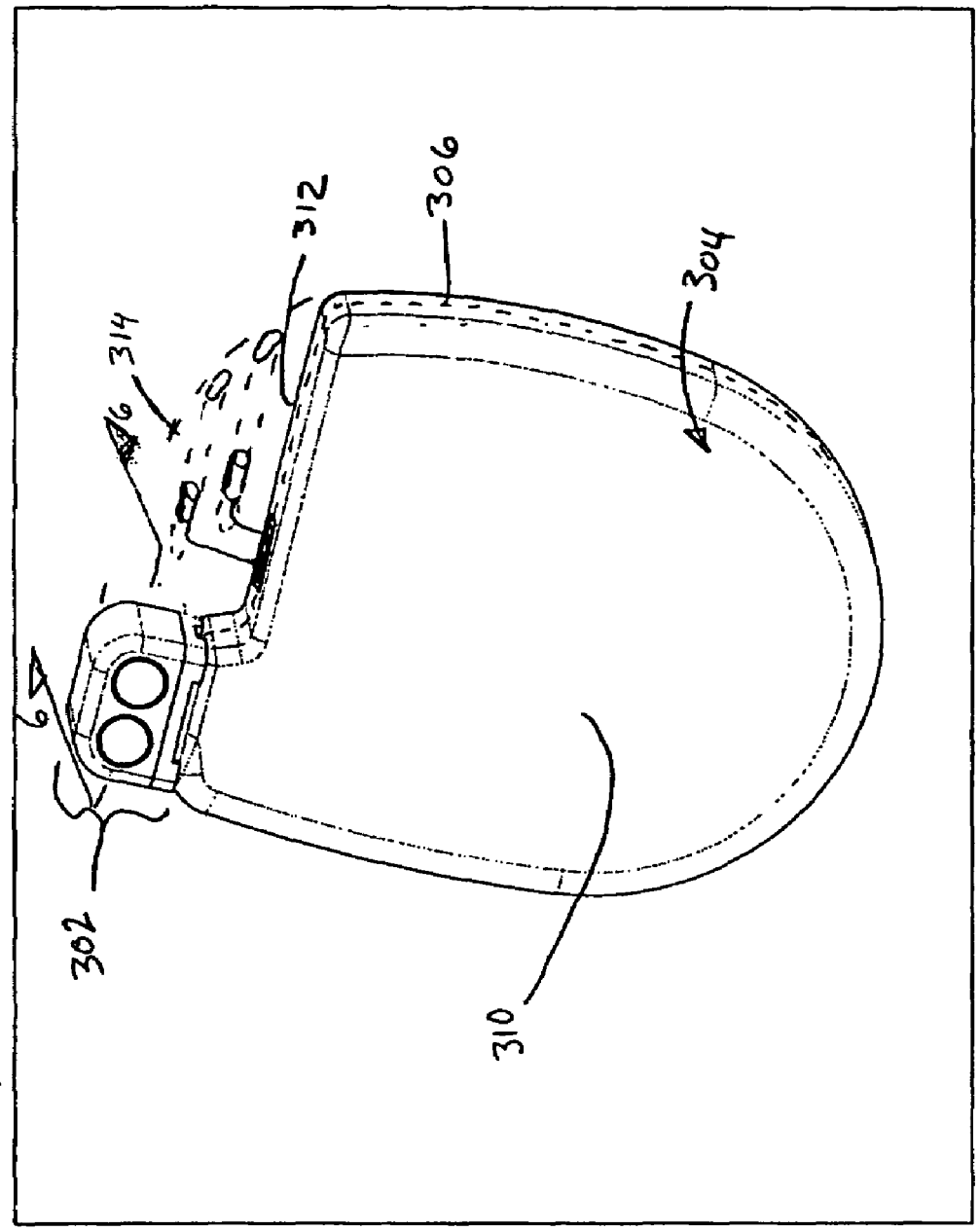

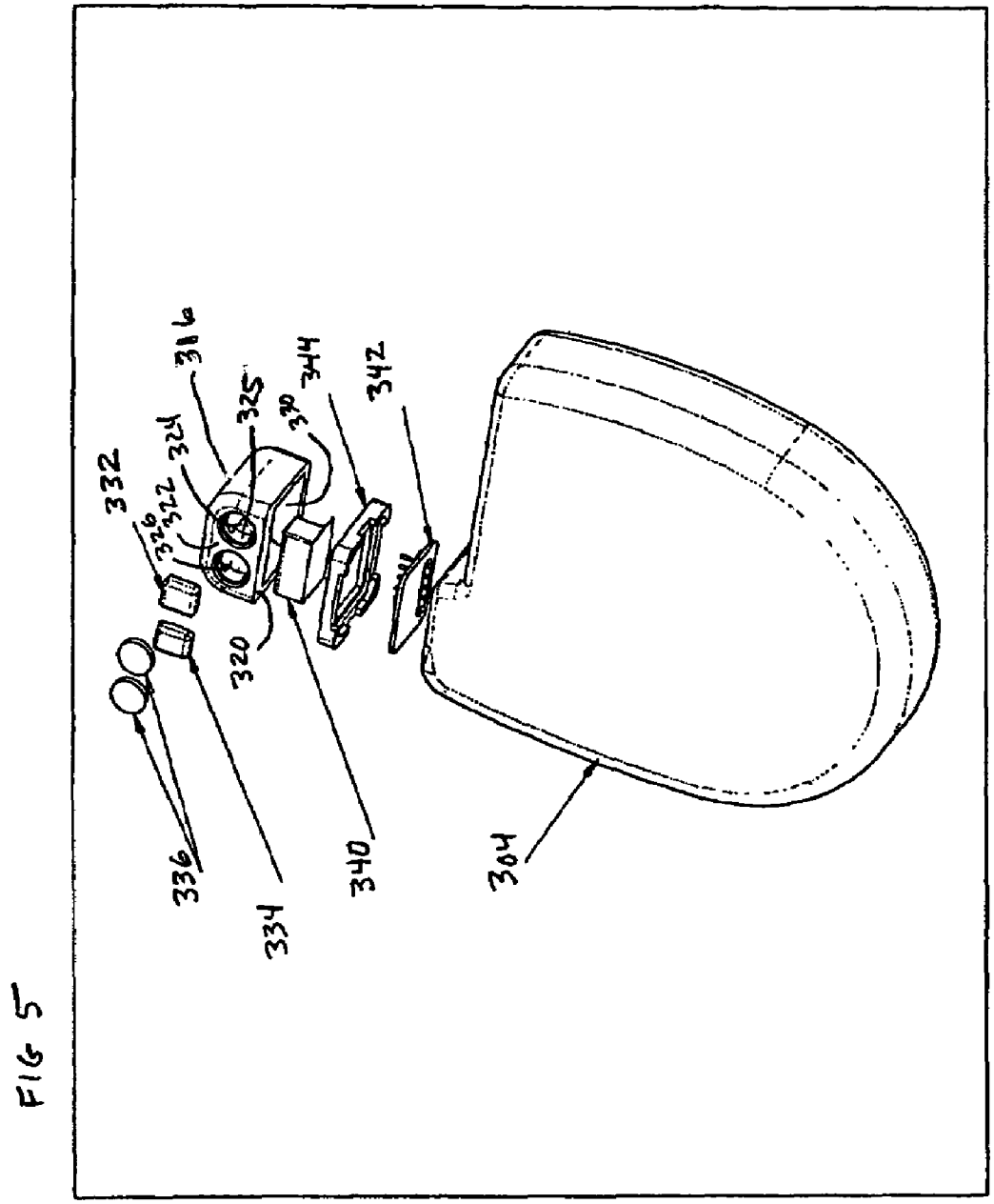

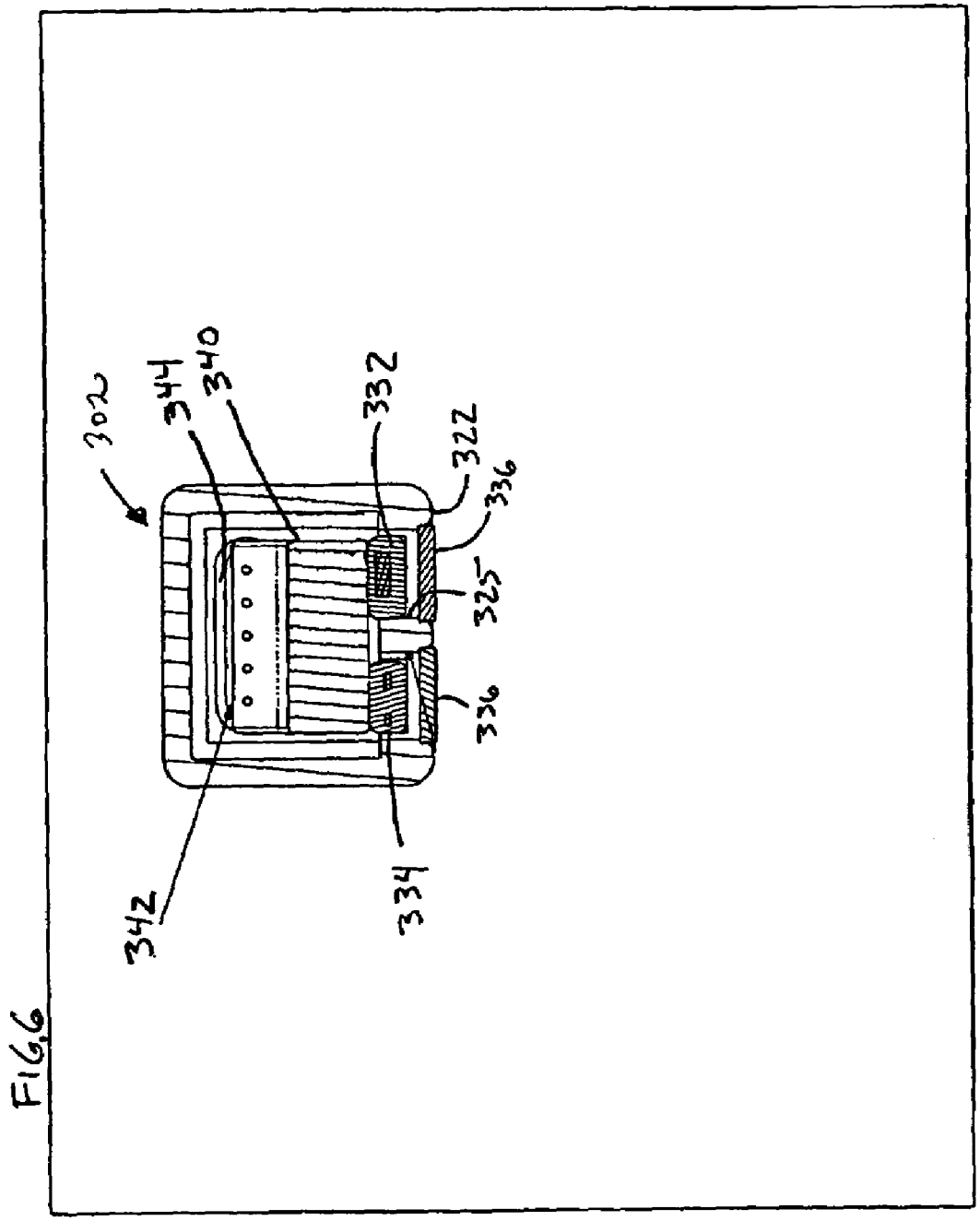

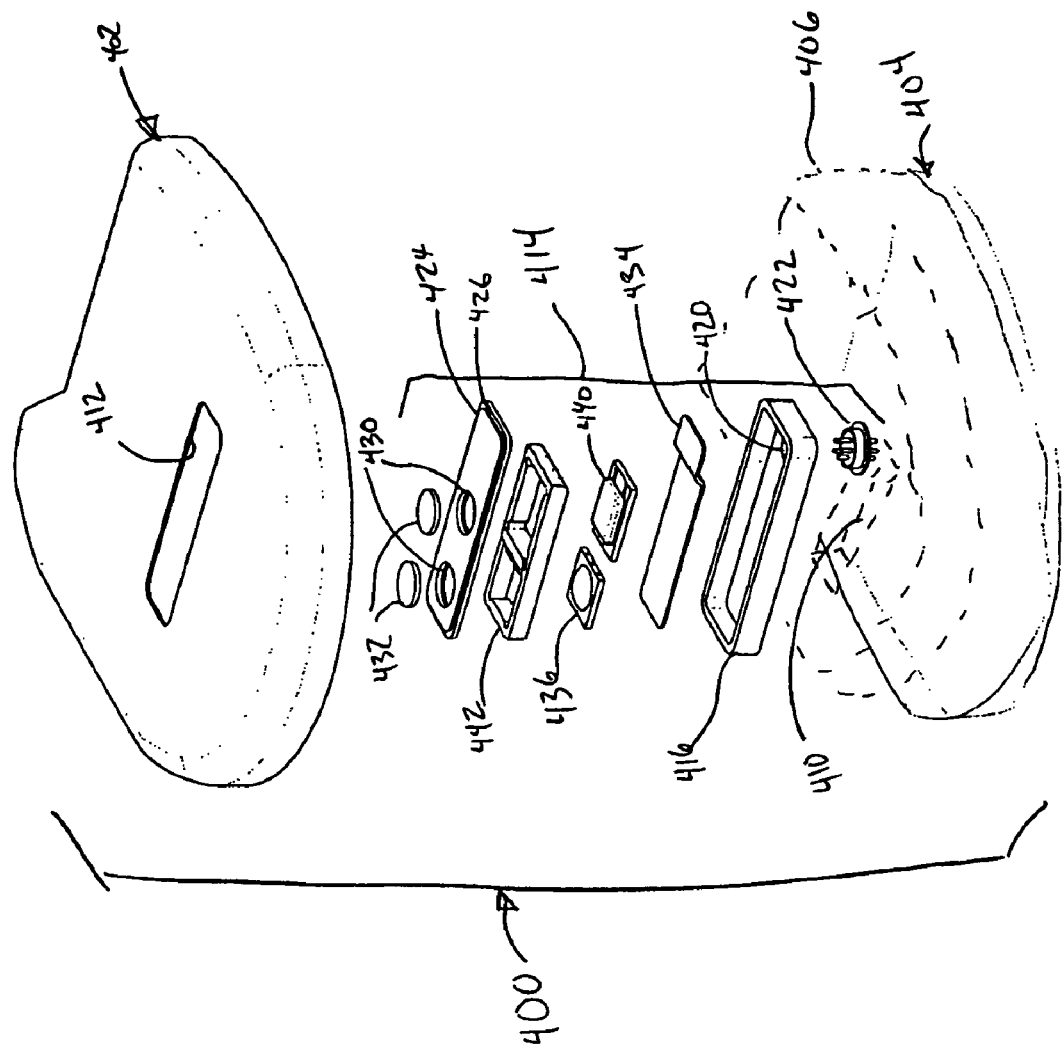

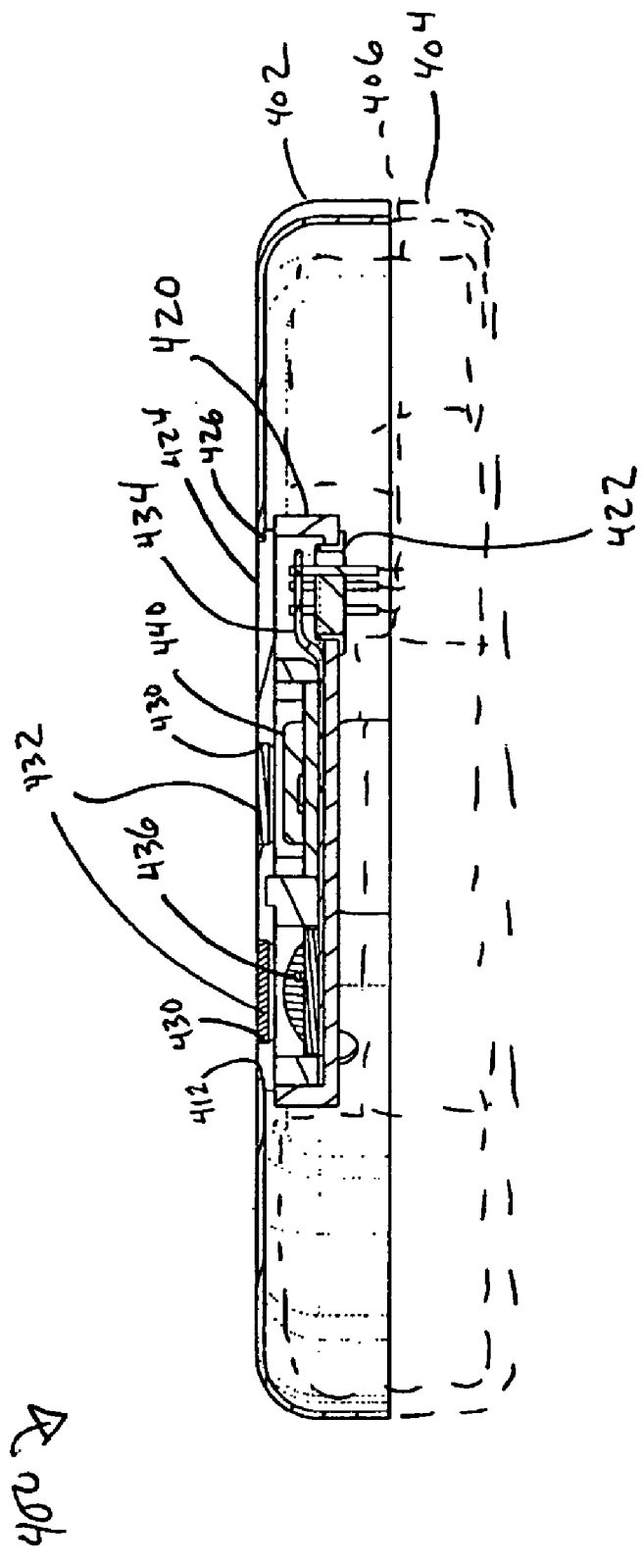

IMPLANTABLE ELECTRONIC MEDICAL DEVICE HAVING AN ENCAPSULATED OPTICAL TRANSDUCER

REFERENCE TO RELATED APPLICATION

This is a Continuation-in-Part of application Ser. No. 10/672,917, filed Sep. 25, 2003, entitled AN IMPLANTABLE ELECTRONIC MEDICAL DEVICE HAVING AN ENCAPSULATED OPTICAL TRANSDUCER, now abandoned.

FIELD OF THE INVENTION

This invention relates to implantable medical devices, and more particularly to those employing photo-plethysmographic sensing.

BACKGROUND OF THE INVENTION

Implantable Cardioverter Defibrillators (ICDs) are implanted in patients susceptible to cardiac tachyarrhythmias including atrial and ventricular tachycardias and atrial and ventricular fibrillation. Such devices typically provide cardioversion or defibrillation by delivering low voltage pacing pulses or high voltage shocks to the patient's heart, typically about 500-800V. The ICD operates by using sensors to detect a fast heart rate or tachyarrhythmia, upon which a battery within the device housing is coupled via an inverter to a high voltage capacitor or capacitor pair to charge the capacitors. When the capacitor reaches a desired voltage, charging is stopped and the capacitors are discharged under control of a microprocessor to provide a therapeutic shock to the patient's heart.

ICDs and other cardiac therapy devices such as pacemakers operate by sensing the cardiac rhythm or pulse rate of the patient in which a device is implanted, in order to detect abnormal rhythms requiring therapy for correction. Current devices provide the sensing function by way of a conductive probe extending from an implanted device to a chamber of the patient's heart, where a free end of the lead has a conductive portion that provides the device with information about the electrical characteristics (e.g. resistance) between the device and the probe tip. While effective, this sensing technique may be substituted or supplemented by the use of photoplethysmography.

Photoplethysmography exploits the nature of some tissue to change its optical characteristics based on cardiac rhythm, with a detectable repeating pattern that follows the pulse. Unlike conventional pulse oximetry, which detects changes in light transmission through tissue such as a fingertip or earlobe based on the characteristics of the blood within the tissue (e.g. oxygen level), photoplethysmography detects blood flow characteristics based on the changing reflective characteristics of the surface of tissue. It has been observed that the vasculature of tissue has changing reflective characteristics of certain wavelengths of light during the cardiac rhythm cycle. (The term "light" is intended to include non-visible electromagnetic radiation such as infra-red.) Specifically, a pulse of decreased reflectivity of red or near infra-red light is observed to correlate with a patent's patient's systolic pulse. This is most readily observed with internal tissue where the vasculature is at the surface, as opposed to external tissue where the vasculature is well below the surface.

The use of photoplethysmography has been found to have limited applications for use with implanted devices. A primary concern is that the technology requires an optically-transmissive "window," while most implanted device circuitry requires a metal housing to prevent external electronic interference from interfering with device operations. The transparent materials available for this window lack the shielding characteristics required to prevent potentially harmful interference. Contemplated alternatives for implantation of separate interconnected devices (one with a metal housing, the other transparent) may create disadvantageous complexity of connections and surgical procedures.

Other prior art devices employ emitters and detectors outside the device housing, but encapsulated by a transparent epoxy material that forms the device header. These suffer the disadvantage that the emitter and detector components are vulnerable to intrusion of body fluids, because an epoxy encapsulation is inadequate to provide a seal against such incursion. Accordingly, such components must be specially selected or manufactured to ensure that they are formed of biocompatible materials that are not degraded by body fluids, and which do not generate harmful materials as a result of such fluid contact that may leach back to body tissues and cause harm. This concern includes exposed lead wires, any required insulation, and materials used for soldering or welding. Conventional cost-effective LED lamps are further believed not to be hermetic, so that internal components must also be selected for biocompatibility, and incur the risk that degradation or failure may occur upon incursion of body fluids.

Devices that include integrated sensors, even if outside of the main hermetically sealed chamber, and with hermetically sealed sensors may have limitations in certain respects. With the complexity of development and assembly of both the sensors and the ICD itself, a fully integrated design can present challenges. Due to ongoing efforts to miniaturize and otherwise improve both ICD circuitry and sensor elements, development of one aspect can affect compatibility with another aspect, necessitating redesigns of the other component. Moreover, with the added complexity of the overall system, there may be an increased yield loss during manufacturing as, for instance, a faulty sensor that is integrated with an ICD may necessitate repair or loss of the entire device.

SUMMARY OF THE INVENTION

The disclosed embodiment overcomes the limitations of the prior art by providing an implantable electronic device. The device has a main housing with a leak-proof-sealed housing chamber containing electronic circuitry. An optical module is connected to the main housing, and has a module housing with a leak-proof-sealed transducer chamber isolated from the main housing chamber. The module housing has an optically-transmissive optical element, and the transducer chamber contains an optical transducer connected to the circuitry. The module housing includes a number of signal conductors extending from the transducer chamber to a location external to the transducer chamber, and connected to circuitry in the main housing chamber.

BRIEF DESCRIPTION OF THE DRAWINGS

Further features and advantages of the present invention may be more readily understood by reference to the following description taken in conjunction with the accompanying drawings, in which:

FIG. 3 is an enlarged sectional view of the device according to a preferred embodiment of the invention.

FIG. 4 is a side view of a first alternative embodiment of the invention.

FIG. 5 is an exploded view of an optical module according to the embodiment of FIG. 4.

FIG. 6 is a perspective view of an optical module according to the embodiment of FIG. 4.

FIG. 7 is an exploded view of a second alternative embodiment of the invention.

FIG. 8 is a sectional side view of the embodiment of FIG. 7.

DETAILED DESCRIPTION OF PREFERRED AND ALTERNATIVE EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
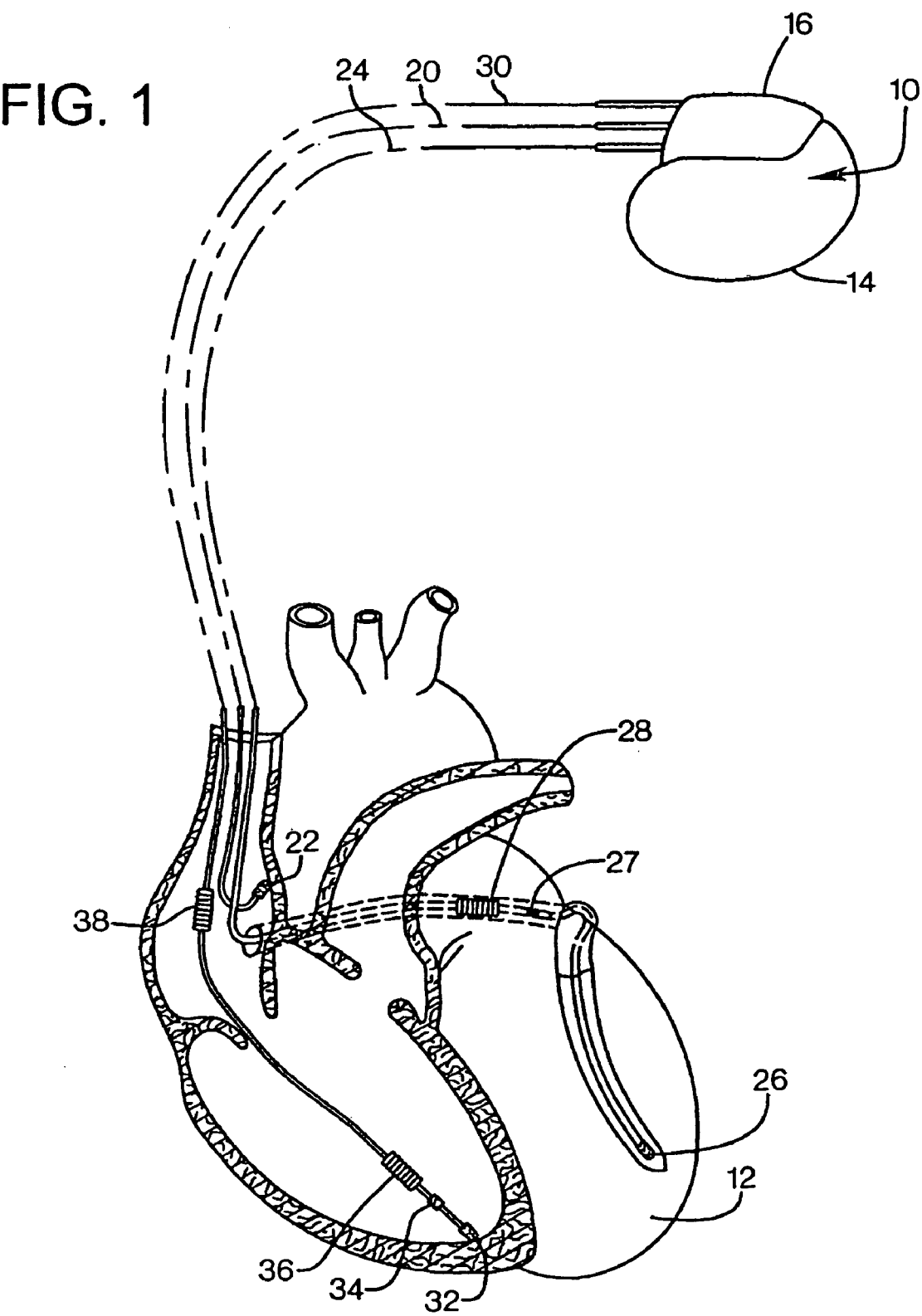
FIG. 1 is a simplified diagram illustrating an implantable stimulation device, in electrical communication with a patient's heart for delivering multi-chamber stimulation and shock therapy.

As shown in FIG. 1, there is a stimulation device 10 consistent with the preferred embodiment of the invention in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The device 10 has a hollow, sealed metal housing 14 containing the circuitry discussed below, and an attached header 16 to which the leads are connected.

To sense left atrial and ventricular cardiac signals and to provide left chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a Superior Vena Cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
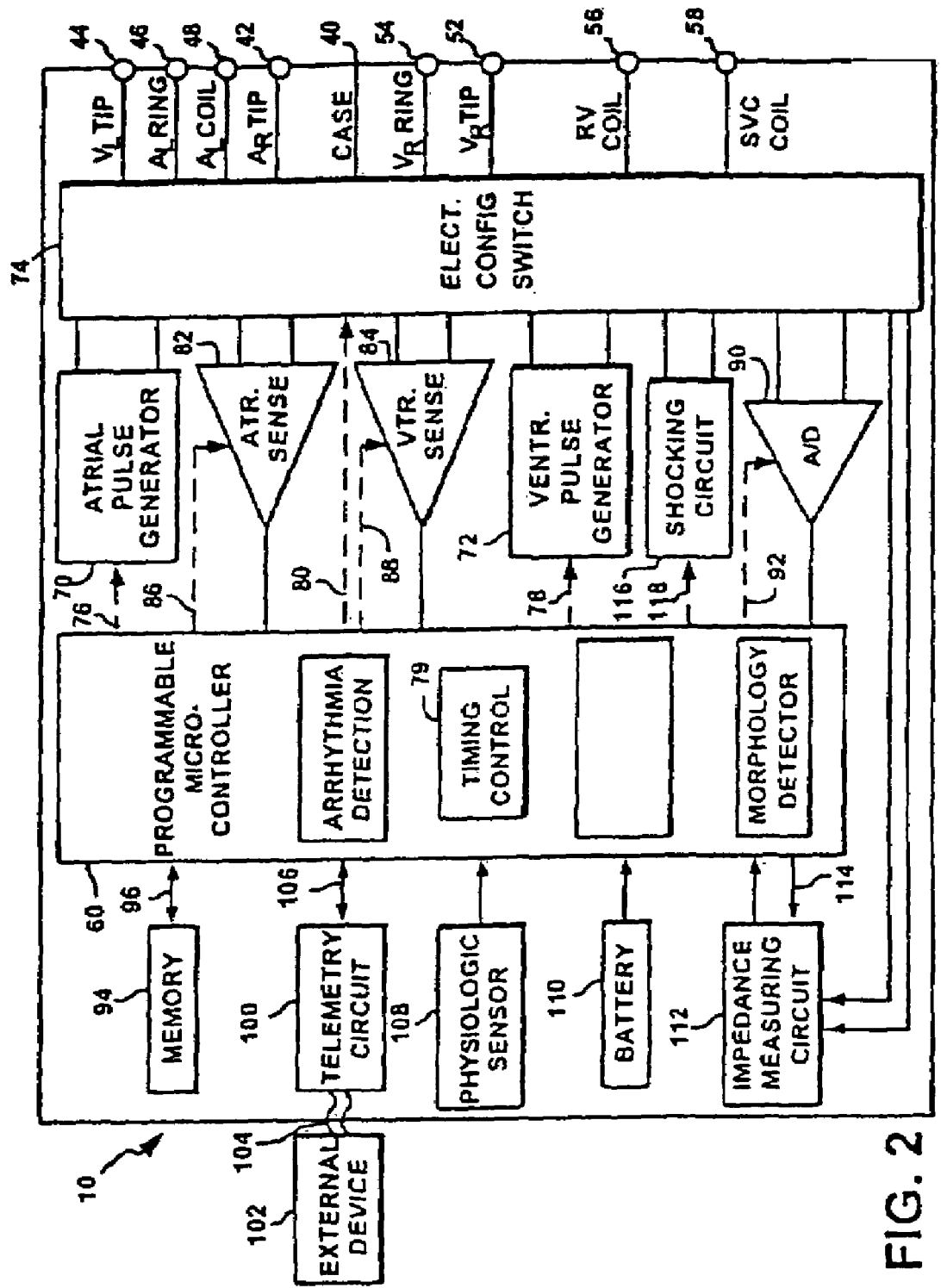
FIG. 2 is a functional block diagram of a multi-chamber implantable stimulation device according to the preferred embodiment illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can," "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Circuitry for sensing the patient's sinus rhythm provides differential amplification (via Op Amps) of the signal received from a photo detector to be described in detail with respect to FIG. 3. The signal then it undergoes A/D conversion to provide a digital signal that can be analyzed by the microprocessor. Numerous alternative digital or analog circuits for sensing a heart rate may be employed.

Conventional atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. As will be discussed and illustrated below, the telemetry circuit is connected to an antenna for communicating with the external device via radio waves with a carrier frequency preferably in the range of 10-15 MHz. In other embodiments, this may range up to or over 100 MHz, subject to government regulation of emitted frequencies. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 μA), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

FIG. 3 illustrates a portion of the device 10 showing the header 16 and a contiguous portion of the housing 14. The housing is a generally flat thin-walled titanium shell (either commercially pure or an alloy such as 6Al4V) with two halves joined at a peripheral seam that forms a line of symmetry along the median of a peripheral wall. The halves are welded together for a hermetic seal.

For this discussion, hermeticity is a term used to describe a well-known standard of permeability to gas or fluid. It is defined in terms of a leak rate of Helium from a pressurized vessel. The acceptable leak rate is less than 10-8 atm_cc/sec of He (or less than 1 cc leaks every 3 years). However, for alternative embodiments, the features and advantages of low permeability may be realized using the principles of the invention by meeting other thresholds of permeability, whether higher or lower. Certain applications may require less-than-hermetic permeability. Other applications may require a stricter threshold above normal hermeticity standards, and these are believed to be achievable by employing the principles of the invention.

For implanted devices such as disclosed herein, the concept of a "leak-proof seal" that does not admit body fluids is important. When a leak-proof seal (which may or may not meet the standards of hermeticity) is provided, components and circuitry that are enclosed by a leak-proof seal are protected against contact with body fluids. This avoids the need to limit enclosed materials to biocompatible materials, which may be unavailable, uneconomical, or otherwise fail to meet device objectives such as performance or size. Fluid contact with normal components is unacceptable because it may harm the function of the components, and fluid may become harmfully contaminated and carry the contaminants back to body tissues. While gas permeability below the threshold of hermeticity are tolerable, fluid leaks are not.

The housing 14 defines a feed-through aperture 200 in the vicinity of the header, and the aperture 200 is defined by a semicircular cutout at the rims of each mating half to form a circular aperture when assembled. A titanium flanged element 202 is welded to the housing to fully occupy the aperture 200. A ceramic insert 206 fully occupies a bore 210 of the flange, and is gold-brazed to the flanged element. A number of separate feed-through wires 212, 214 are closely received in small separate bores 216 in the insert, and gold-brazed to the insert to provide a hermetic seal.

Together, the wires, insert, and flange element provide a leak-proof seal of the housing at the aperture 200. In the preferred embodiment, the disclosed manufacturing techniques provide a hermetic seal. The wires extend from the feed-through to metal sleeves 218 that will receive the ends of the leads. (Two sleeves are shown for clarity, while three or more sleeves may be provided to accommodate the needed number of leads.) The wires are formed of a platinum-iridium alloy, which is biocompatible to avoid corrosion when contacted by tissue and body fluids. The wires are connected at the interior of the housing to sensing and therapy circuitry as discussed above. The conductive sleeves and feed-through are encapsulated in epoxy to form the header 16. The header defines several bores 220 that align with the sleeves to receive the leads.

An optical photoplethysmographic module 222 is connected to the housing at a module aperture 224 defined in a side wall of the housing at the seam, with a circular aperture defined by a semi-circular cut-out on each half of the housing. A titanium flanged ring 226 is welded to the housing. The ring defines a large central bore 230. The periphery of the flange defines a circular groove 234 that encircles the bore 230.

A ceramic insert 236 fully occupies the bore 230 of the ring, to which it is gold-brazed to provide a hermetic seal. An optical emitter element 240 and an optical detector element 242 are connected to the insert 236. In the preferred embodiment, each of the emitter and detector has an encapsulated end portion 244 with a pair of leads 246 extending parallel to each other. These are preferably standard LED devices to provide low component cost, with wire leadframes having non-leak-proof epoxy-encapsulated end portions. The encapsulated end portions contain the optical transducers, and are positioned externally of the housing. The leads extend through the insert, closely received in small separate bores in the insert, and are gold-brazed to the insert to provide a hermetic seal. Together, the wires, insert, and flange element provide a leak-proof seal of the housing at the aperture 224. The seal is hermetic in the preferred embodiment. The insert is preferably plated with a conductive material that extends to the ring in all directions, covering an entire surface of the insert on at least one side of the ring (except for minimal clearance to avoid shorting the leads as discussed below.) This provides a shield against electromagnetic interference (EMI) that would otherwise pass through the aperture in the housing.

In the preferred embodiment, the emitter is a dual wavelength light emitting diode (LED) or two separate diodes each of a different wavelength. The wavelengths of the preferred embodiment are 660 and 940 nm. A single wavelength may be used for basic photo-plethysmography, and the second wavelength allows the same transducer to be employed for pulse oximetry if desired. These two light sources alternate between being on and off, however, each would operate at a duty cycle well below 50%. In alternative embodiments, the wavelength may range between about 600 and 1000 nm, with infrared and visible wavelengths being considered as "light" for the purposes of this disclosure. An emission wavelength of 905 nm has proven suitable in single-wavelength embodiments. The detector is a photo-detector encapsulated in a similar lamp package as the LED, with a wavelength sensitivity matched to the wavelength of the source.

A transparent optical housing element or dome 250 has an elongated cylindrical shape with a circular cross section. The dome element is closed at one end, and open at a free end to define a circular rim 241. The rim is closely received in the ring bore 230, and gold-brazed therein to provide a hermetic seal. Together, the dome 250, ring 226, and insert 236 define a leak-proof optical chamber 252 that contains the emitter and detector. The chamber is leak-proof with respect to the exterior of the device, and with respect to the housing chamber.

An opaque barrier 254 within the optical chamber is positioned between the active portions of the emitter and detector, to prevent the detector from receiving light directly from the emitter, and limiting detected light to that reflected from tissue external to the optical housing.

The dome element is formed of a material with several important qualities. It is biocompatible, so that it is neither degraded by body fluids, nor does it have an adverse effect on tissues. In the preferred embodiment, the material has a low permeability that makes it hermetic. The material does not significantly attenuate or scatter light waves within the useful range. Examples of suitable materials include quartz and glass. These are all non-metallic, and fully biocompatible. They also are suitable for brazing to the titanium flange to provide the desired leak-proof seal (alternatively, they may be hermetically attached by fusing the rim to an anchor feature on the ring.) The surface finish of the dome is preferably optically smooth, to avoid light scattering at either dome surface. However, some surface roughness that may appear to generate a frosted appearance or limited light scattering may be tolerable. Similarly, the dome material may be non-transparent with limited translucency and yield a functional device.

The dome need not be fully hermetic as provided by the preferred embodiment. A leak-proof seal that excludes body fluids but which is not fully hermetic may be suitable. A hermetic seal of the device housing 14 is preferred at the aperture 224. In such non-hermetic embodiments, a silicone seal between the dome and ring may be used instead of the gold brazing used for hermeticity. Also, some light-transmissive plastics and epoxy materials may be used for the dome material, and the dome chamber may be evacuated, gas-filled, or filled by a light-transmissive encapsulant such as epoxy or silicone. Another suitable dome material for certain embodiments is an optical quality thermoplastic elastomer such as Tecothane.

For simplicity and clarity, the emitter and detector are shown with parallel axes, with an axis of emission and detection extending to the right as illustrated in FIG. 3. In a wide array of alternative arrangements, the emitter and detector may be positioned differently. For instance, they may be bent at a right angle to point upward, or to point into or out of the plane of the Figure. The emitter and detector may also be encapsulated in separate packages, or need not be encapsulated at all, as long as they are made of or protected by a biocompatible material. It is important that at least some of the light emitted reach a tissue surface adjacent to the dome or transparent header, and that some of that light be scattered or reflected toward the detector. In the preferred embodiment, the adjacent tissue is in optically immersive contact with the outside surface of the dome or header.

In the preferred embodiment, the dome 250 is located adjacent to the feed-through in a recessed portion of the housing. Consequently, the dome and feed-through can both be encapsulated within the common header 16. However, in alternative embodiments, and header may be shaped as a smaller header 16', which encapsulates only the sleeves 218, but not the dome. Other alternatives may provide an encapsulated dome at a different location on the housing from the header, so that the encapsulation provides mechanical protection and a smooth profile without impairing optical transmission, and while the dome maintains hermeticity.

The lead wires 246 are connected at the interior of the housing to the sensing circuitry discussed above, either in addition to the sensing capabilities provided by endocardial leads, or as a substitute.

MODULAR EMBODIMENTS

FIG. 4 shows an alternative ICD 300 with an optical sensor module 302. The ICD 300 has a main housing 304 having a generally planar shape with a curved peripheral profile. The main housing 304 is formed of two clamshell-like halves joined by a weld line 306 at the periphery. Each half has a flat major face 310 facing in opposite directions, parallel to each other. The housing periphery has a flat indented portion 312 in which is received a header 314. The header provides a generally continuously curved periphery with the rest of the housing. In this embodiment, the header may be of a material with unconstrained optical properties; transparent material is not required because the header has no optical function unless it is desired to visualize the insertion of leads. The optical sensor module 302 is positioned adjacent to the header at the housing periphery. The header and optical module are contained between the major planes of the main housing halves. The location of the module is space efficient, because it utilizes space that is unused in current ICD designs. However, in alternative embodiments, the sensor can be placed anywhere external to the ICD case where it can be connected to a feedthrough.

As shown in FIG. 5, the sensor module 302 has a sensor module housing 316 that is an alumina shell of roughly cubical shape, with rounded corners. The alumina material selected for the housing is biocompatible and allows for hermetic sealing, to both the seal band feedthrough connector and to the optical windows, as will be discussed below. Another advantage of the housing material is that it can be molded into a wide range of shapes. Because the module forms a peripheral portion of the device, patient comfort is a concern. Because alumina can be molded, the smoother features desired for patient comfort can be easily produced.

The module housing has a bottom surface 320 that is generally flat. A first side surface 322 defines a pair of apertures 324, 326 that communicate with a bottom cavity 330 defined in the bottom surface 320. A dual-wavelength LED 332 resides within the module housing adjacent to the first aperture 324, and a photodiode 334 resides within the module housing adjacent to the second aperture 326, with the two apertures separated by an opaque portion 325 of the housing.

Two sapphire optical windows 336 are sized to closely fit the apertures, which are rabbeted with a small ledge on which the windows rest. This ledge allow for easier manufacturing of the part as it does not need to be held during the sealing process. The LED and photodiode are mounted to and electrically connected to a circuit element 340 that is preferably a flexible flex circuit folded into the articulated shape shown. A feedthrough connector 342 is a flat rectangular ceramic element with several independent conductors passing through it. The feedthrough provides several electrical lines isolated from each other for connection to the flex circuit, and is sized to seal an aperture on the bottom cavity for a hermetic seal of the module housing. A titanium seal band 344 is sized to encompass the housing at the bottom surface, with a profile the same as the module housing, and a flat upper surface to abut the lower surface 320 of the module housing.

The LED and photodiode are mounted coplanar in the housing to transmit and receive light to and from a common point external of and at close range to the module housing. The windows are biocompatible sapphire material that allows the light to be transmitted with little attenuation into the subcutaneous tissue and reflected back to be measured by the photodiode. The optical windows are preferably hermetically sealed to the housing a high heat 99.9% gold braze. The Ti seal band to the alumina housing is also high heat gold braze. This should also happen before electrical components are installed. Because this high heat process can damage the electrical components, the window-brazing process is performed before the components are installed. This is why the housing is designed as a hollow shell rather than a solid case with cavities for the components. With a hollow shell the components can all be placed inside after the high heat sealing process. In addition, the seal band 344 is also brazed to the housing prior to component installation.

The flex circuit is assembled, with the emitter 334 and detector 332 soldered to the circuit. The feedthrough conductors are also soldered to the circuit to finish the assembly, which is then installed in the module housing with the emitter and detectors inserted into the respective apertures as shown in FIG. 6. After the electrical circuit assembly has been installed, the feedthrough perimeter is laser welded (a relatively low heat process) to the seal band. This seals the module housing to provide a complete, hermetically sealed unit that is tested for function and performance.

At this stage, the main housing has been populated with all the internal circuitry and components, then welded at the peripheral seam. An aperture remains at the peripheral housing portion beneath where the module is to reside. After testing of the module, a lower-temperature heat sealing technique such as laser welding or resistance is used to make the electrical connections between the ICD wires and the module wires. The cutouts designed into the seal band allow access for laser or resistance welding. After welding, the gap between the them can be filled with epoxy.

In an alternative embodiment, the main housing may be fully sealed, with a feedthrough where the module is to be mounted, so that the respective feedthrough conductors are connected to each other. Otherwise, in the preferred embodiment, circuit elements or wires extend from main ICD circuitry, and are connected to the module feedthrough leads. The titanium seal band facilitates a low temperature sealing process. It is brazed to the main housing in a welding process at a lower temperature than the gold brazing used before the installation of components. The flex circuit/board connects the LED and photodiode to the titanium feedthrough assembly, which exits the module housing to make an electrical connection with electrical lines from the ICD. Alternatively, the ICD main housing may include a feedthrough that carries these lines for connection to the module, and which provides a hermetic seal of the module.

The optical sensor module is a hermetically sealed sub-assembly that is located external to the main housing. In addition to modular manufacturing advantages, the module design may be improved and reengineered, as technology advances can be implemented with a simple substitution of the module on an existing ICD design. The module can be integrated into the ICD at the last step after the ICD case has been sealed. The module is easily integrated to the ICD via its feedthrough adapter that can be connected and laser welded to existing feedthrough designs to make an electrical connection. As with current injection molded headers, the module can then be backfilled to seal any gaps between the assembly and the ICD.

FIG. 7 shows an additional alternative embodiment ICD 400 having a two-part titanium main housing formed of an upper half 402 and a lower half 404. The housing has the generally flat shape with curved periphery (with indent for the header) as in the embodiment above. The housing contains ICD circuitry, shown for simplicity as block 406. The circuitry largely occupies the volume defined by the housing halves, except for an elongated rectangular recess volume 410 defined within the circuitry block. The upper housing half defines an elongated rectangular aperture 412 that is registered with and sized similar to the recess 410.

The ICD 400 includes an optical module 414 that occupies the recess in the circuitry when the OICD is assembled, and which also occupies and hermetically seals the housing aperture 412. The optical module includes a titanium sensor module housing 416 having the shape of a shallow elongated rectangular box with a periphery shaped to be closely received within the circuit recess 410. The housing 416 has a periphery slightly larger than the housing aperture 412. A rear circular aperture 420 in the module housing closely receives a feedthrough element 422 containing several isolated conductors for a hermetic seal, as discussed above.

A titanium module housing cover or lid 424 is sized to cover the upper rim of the module housing 416 to enclose a module chamber. The lid has a rabbeted upper peripheral edge 426, so that the upper surface closely fits in the main housing aperture 412, and the lower flange formed by the rabbet rests against the interior of the upper main housing half 402 as shown best in FIG. 8. The lid defines a pair of circular apertures 430, which are rabbeted to closely receive and support transparent windows 432 with a hermetic seal. The process to create this hermetic seal uses a pure gold braze. A thin ring of gold is placed around the sapphire window and within the circular cutout in the titanium. Then the titanium lid assembly is placed in an oven at about 2000° F. so that the gold melts and bonds with the titanium and sapphire. The outer perimeter of the sapphire windows are also pre-metallized with gold to aide the brazing process.

Within the module, a flexible circuit element 434 has conductive traces that connect to the feedthrough, and to an LED emitter 436 and a photodiode 440 mounted on the flex circuit. An opaque frame 442 surrounds the LED and the photodiode to optically isolate them from each other, and extends from the surface of the flex circuit to the rear surface of the lid. The LED, is a set of two LEDs of different wavelengths (typically red and IR) in a single unit package. In alternative embodiments, the LED may be in the form of two units, one for each wavelength.

The optical sensor module is designed as a hermetically sealed, "drop-in" sub-assembly that is fully manufactured and sealed, then electrically tested to assure performance.

Then, it is laser welded into the face of the ICD case via the cut-out in the case. The module lid provides a hermetic seal of the main housing, and itself also hermetically seals the module contents from the main housing and from the exterior of the device. The process of laser welding the module to the device preserves the hermeticity requirement of the ICD device and provides a simple means for mechanically and hermetically integrating the module to the device. The module is contained within the volume of the device but not within the same environment. The ability to complete and test the module prior to connection and installation in the ICD provides the advantages noted above. Moreover, the flush nature of the module at one of the major faces of the housing preserves patient comfort by not adding any components beyond the peripheral and planar envelope of the device.

In this embodiment, the LEDs and photodiode are mounted coplanar in the holder. In alternative embodiments, they may be aimed with some relative angle toward a common external point to transmit and receive light to and from the common point. The optical windows are a biocompatible transparent material such as sapphire or quartz, and are hermetically sealed into the titanium cover by the process of brazing with pure gold. The lid is then welded to the module housing to maintain device biocompatibility and hermeticity requirements. The use of titanium for the module housing permits it to be welded to the ICD case, and provides shielding from EMI (electro-magnetic interference) and RFI (radio frequency interference) in addition to the hermetic seal.

The above several embodiments include numerous features and details common among themselves, except for the various distinct features specifically noted. Where an embodiment is not described as having certain features, it may be assumed to have any of the comparable features of any of the other embodiments. Further, where technically practical, the various features of the embodiments may be combined in any suitable permutation.

The invention claimed is:

1. An implantable electronic device comprising:
   a main housing defining a leak-proof-sealed housing chamber containing electronic circuitry;
   a header connected to the main housing;
   an optical module connected to remain in contact with the main housing;
   the optical module having a module housing defining a leak-proof-sealed transducer chamber isolated from the main housing chamber and the header;
   the module housing having an optically-transmissive optical element;
   the transducer chamber containing an optical transducer connected to the circuitry; and
   the module housing including a plurality of signal conductors extending from the transducer chamber to a location external of the transducer chamber, and connected to circuitry in the main housing chamber.

2. The device of claim 1 wherein the main housing defines an aperture, and wherein the module housing occupies the aperture and is sealed to the main housing aperture to seal the main housing chamber.

3. The device of claim 2 wherein the main housing has a planar shape with two opposed major faces, and wherein the aperture is defined in one of the major faces.

4. The device of claim 3 wherein the module has a major face flush with the major face of the main housing in which the aperture is defined.

5. The device of claim 1 wherein the main housing includes a connector element operably connected to the signal conductors and having conductors extending into the main housing chamber.

6. The device of claim 5 wherein the connector element sealably occupies an aperture in the main housing.

7. The device of claim 1 wherein the main housing comprises two major portions, and wherein the aperture is defined entirely within one of the major portions.

8. The device of claim 1 wherein the main housing has a generally planar shape, and the header defines lead apertures at a peripheral portion of the main housing, the module being adjacent to the header.

9. The device of claim 1 wherein the module is external to the header.

10. The device of claim 1 wherein the optically transmissive element is apart from the header.

11. The device of claim 8 wherein the optically transmissive element is positioned in a plane defined by a major surface of the main housing.

12. The device of claim 1 further comprising a flange connected to the main housing.

13. The device of claim 12 wherein the flange is a flanged ring and wherein the ring defines a bore, the device further comprising an insert connected to the bore.

14. The device of claim 13 wherein the insert comprises ceramic.

15. The device of claim 13 wherein the insert fully occupies the bore and wherein the insert is gold-blazed to the bore to provide a hermetic seal.

16. The device of claim 13 wherein the plurality of signal conductors are connected to the insert to provide a hermetic seal.

17. The device of claim 13, wherein the insert is plated with a conductive material to provide a shield against electromagnetic interference.

18. The device of claim 1 wherein the optically-transmissive optical element comprises a wire leadframe having an encapsulated end portion, the encapsulated end portion housing the optical transducer.

19. The device of claim 13 wherein the module housing is closed at one end and open at a free end to define a rim and wherein the module housing is hermetically sealed to the bore.

20. The device of claim 1 wherein the module housing is hermetic.

* * * * *